United States Patent [19]

Holmes et al.

[11] Patent Number: 5,336,238
[45] Date of Patent: Aug. 9, 1994

[54] SURGICAL INSTURMENT CAPABLE OF DISASSEMBLY

[75] Inventors: J. Stephen Holmes, Atlanta; Timothy Lamartina, Lawrenceville, both of Ga.

[73] Assignee: Birtcher Medical Systems, Inc., Irvine, Calif.

[21] Appl. No.: 93,477

[22] Filed: Jul. 19, 1993

[51] Int. Cl.5 .............................................. A61B 17/28
[52] U.S. Cl. .................................. 606/208; 606/170; 606/205; 81/416
[58] Field of Search ............... 606/205, 206, 207, 208, 606/170, 174; 128/751; 81/416

[56] References Cited

U.S. PATENT DOCUMENTS

| | | |
|---|---|---|
| 2,113,246 | 4/1938 | Wappler . |
| 3,870,048 | 3/1975 | Yoon . |
| 3,964,468 | 6/1976 | Schulz . |
| 4,085,743 | 4/1978 | Yoon . |
| 4,369,788 | 1/1983 | Goald . |
| 4,427,014 | 1/1984 | Bel et al. . |
| 4,569,131 | 2/1986 | Falk et al. . |
| 4,760,848 | 8/1988 | Hasson . |
| 4,763,668 | 8/1988 | Macek et al. . |
| 4,962,770 | 10/1990 | Agee et al. . |
| 4,982,727 | 1/1991 | Sato . |
| 5,133,735 | 7/1992 | Slater et al. . |
| 5,133,736 | 7/1992 | Bales, Jr. et al. . |

Primary Examiner—Michael H. Thaler
Attorney, Agent, or Firm—Rodgers & Rodgers

[57] ABSTRACT

A surgical instrument which easily disassembles for sterilization comprises an inner rod coaxially disposed in a hollow tube with a handle at one end of the rod and a working tip at the other end. The handle is detachably interconnected to the inner rod and the inner rod is detachably interconnected to the hollow tube by means of at least one locking pin.

7 Claims, 2 Drawing Sheets

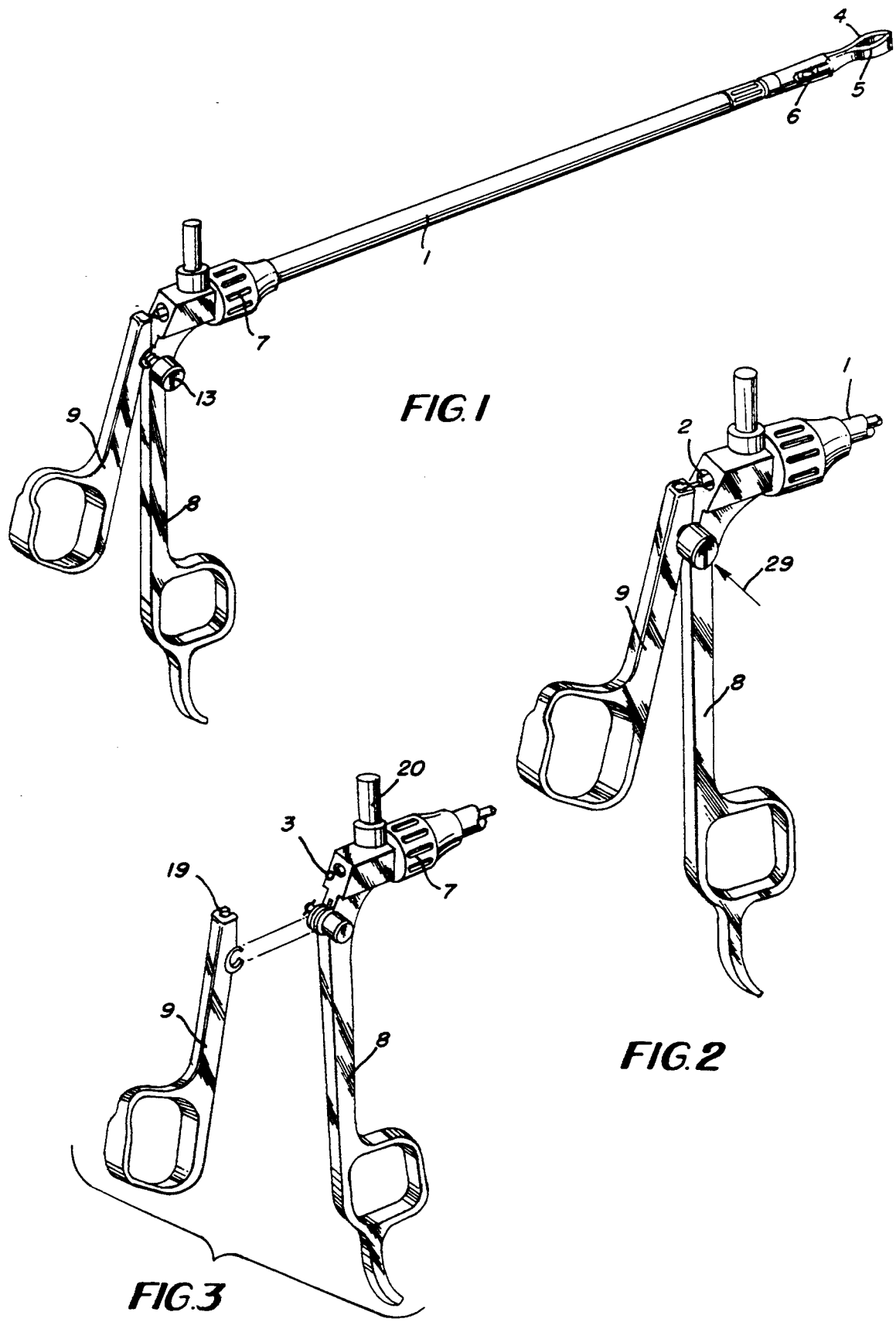

SURGICAL INSTURMENT CAPABLE OF DISASSEMBLY

BACKGROUND OF THE INVENTION

This invention relates generally to surgical instruments for use in minimally invasive surgical procedures. Up until recently, most abdominal and thoracic procedures required major incisions in order to provide an ability to observe the body cavity and perform any necessary diagnosis and treatment. In general, instruments used in these procedures are of the closed shaft variety. Since these instruments cannot be disassembled, complete sterilization is not possible because microscopic pockets of tissue and blood are often left on the instrument even after completion of accepted sterilization procedures.

In order to insure complete sterilization of a surgical instrument, the instrument must essentially be capable of disassembly into its major components. This insures that all surfaces of the instrument are exposed to the particular sterilization medium and any concern that the instrument is not thoroughly sterilized is thereby eliminated.

SUMMARY OF THE INVENTION

By this invention, a surgical instrument is provided and comprises an inner rod coaxially disposed within a hollow tube and which has a working tip at the distal end and a handle at the proximal end and wherein the handle is detachably interconnected to the inner rod. A collet is coaxially and reciprocally disposed with respect to the hollow tube whereby movement of the collet in one direction deactivates locking means and causes the inner rod to be released with respect to the hollow tube.

BRIEF DESCRIPTION OF THE DRAWINGS

In the drawings,

FIG. 1 is a perspective view of a surgical instrument capable of disassembly according to this invention;

FIG. 2 is a perspective view of the instrument handle;

FIG. 3 is a perspective view of the handle in disassembled condition;

DESCRIPTION OF THE PREFERRED EMBODIMENT

Figure 4:
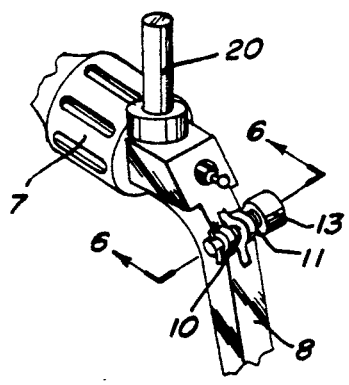
FIG. 4 is a perspective view of the handle release means.

In the drawings, the numeral 1 designates the outer hollow tub of the surgical instrument and the numeral 2 identifies the inner rod which has locking ball 3 disposed at one end thereof. The working tip of the instrument is disposed at the distal end thereof and comprises jaws 4 and 5 which are opened and closed by means of linkage mechanism 6, as is well known.

Disposed at the proximal end of the instrument and secured to hollow tube 1 is rotation knob 7. In order to facilitate a 360 degree rotation of jaws 4 and 5, rotation knob 7 is pivotally mounted on handle element 8.

Figure 6:
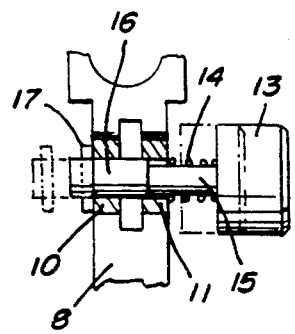
FIG. 6 is a sectional view taken along the line 6—6 in FIG. 4.
Figure 7:
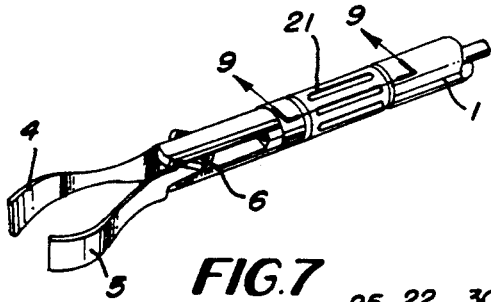
FIGS. 7 and 8 are perspective views of the distal end of the instrument.
Figure 8:
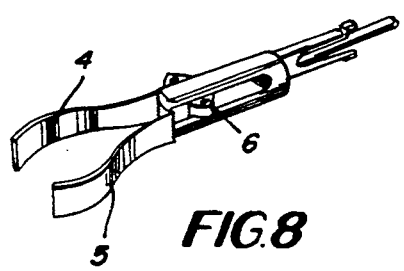

Handle element 9 is detachably connected to handle element 8 by locking means best shown in FIG. 6. More specifically, the locking means comprises closed rings 10 and 11 integrally formed on handle element 8 and partially closed ring 12 integrally formed on handle element 9. Knob 13 is biased outwardly of the handle means or to the right, as viewed in FIG. 6, by means of compression spring 14. Attached to knob 13 is a locking rod which comprises an inner portion 15 which is of smaller diameter than associated outer portion 16. Retaining pin 17 is secured on the end of the locking rod remote from knob 13 and acts to prevent the locking rod from disengagement from the instrument handle means.

Figure 5:
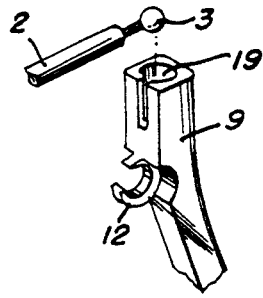
FIG. 5 is a perspective view of the means for interconnecting the handle and the inner rod.

As best shown in FIG. 5, means is provided to interconnect inner rod 2 and handle element 9. Specifically, inner rod 2 extends through aperture 18 of handle element 8 and forms an operably interconnected relationship with respect to handle element 9 by the interlocked disposition of ball 3 being disposed in slot 19. Of course, operation of handles 8 and 9, in known manner, results in the activation of linkage mechanism 6 thereby causing jaws 4 and 5 to open and close as desired.

As is well known, monopolar post 20 is formed on the upper surface of handle element 8 at the proximal end of the instrument. Also, in order to improve the comfort and operability of the instrument, the handle itself is made of an ergonomic configuration.

Figure 9:
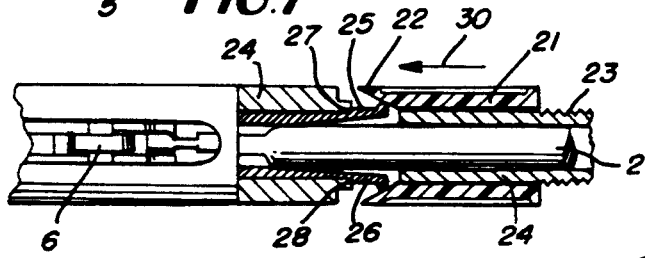
FIG. 9 is a sectional view taken along the line 9—9 in FIG. 7.

According to this invention, inner rod 2 and the associated working tip of the instrument are disjointably connected to hollow tube 1 by means of a collet mechanism. Specifically, collet 21 is rotatable about inner rod 2 independently of hollow tube 1 and comprises bevelled surface 22 at one end thereof. Externally threaded end 23 of attachment housing 24 is engageable with internal threads formed on the distal end of hollow tube 1. As best shown in FIG. 9, locking pins 25 and 26 are attached to the housing for linking mechanism 6 in a spring-like fashion and are provided, respectively, with notches 27 and 28 and which are disposed in openings formed in attachment housing 24 whereby notches 27 and 28 engage attachment housing 24.

Figure 10:
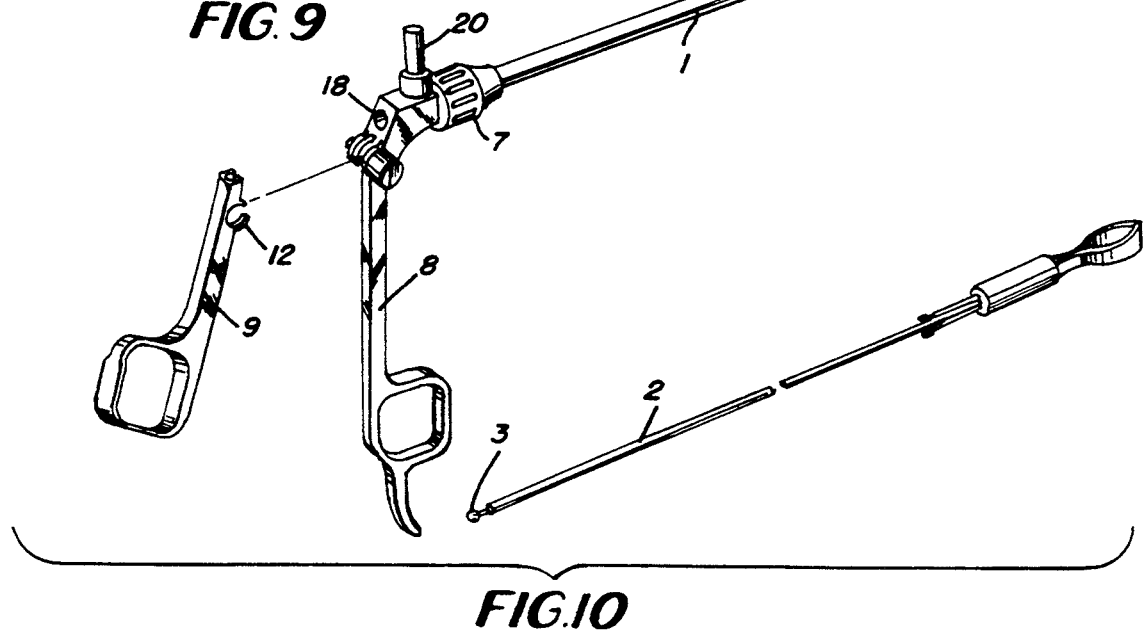
FIG. 10 is a perspective view of the instrument in disassembled condition.

In order to disassemble the fully assembled instrument, as shown in FIG. 1, into the fully disassembled instrument, as shown in FIG. 10, initially knob 13 is pushed inwardly of the handle as indicated by arrow 29 in FIG. 2. This causes the smaller diameter portion 15 of the locking rod to move to the left, as viewed in FIG. 6, thus allowing the open segment of ring 12 to slip past portion 15 and thereby resulting in the separation of handle elements 8 and 9 into the condition shown in FIG. 3. When knob 13 is disposed in its normal outwardly biased position, as depicted in solid lines in FIG. 6, outer portion 16 is of sufficiently large diameter so as to maintain ring 12 in an interlocked condition therewith. Simultaneously with the separation of handle elements 8 and 9, ball 3 is maneuvered out of slot 19, as best viewed in FIG. 5.

Following this operation, collet 21 is manually pushed toward the distal end of the instrument, as indicated by arrow 30 in FIG. 9, so as to cause the ends of locking pins 25 and 26 to slide along bevelled surface 22 of collet 21 thereby compressing locking pins 25 and 26 inwardly with respect to inner rod 2 a sufficient distance to allow notches 27 and 28 to disengage attachment housing 24. Inner rod 2 and the associated working tip of the instrument can then be easily disassembled whereby ball 3 is withdrawn initially through aperture 18 and then inner rod 2 is pulled all the way through hollow tube 1. The instrument is then disposed in a disassembled condition as shown in FIG. 10.

Following disassembly, the individual elements of the instrument are conveniently and thoroughly sterilized by means of accepted sterilization procedures. The instrument is then reassembled by inserting inner rod 2 through hollow tube 1 and aperture 18 wherein ball 3 is simply inserted into slot 19. Knob 13 is then depressed thereby allowing ring 12 to be positioned around portion 15 of the locking rod. Simultaneously with this operation, locking pins 25 and 26 are interlocked with attachment housing 24 by means of notches 27 and 28. When knob 13 is released, portion 16 enters ring 12 thereby securing the instrument in a completely assembled condition whereby it is ready for reuse in an appropriate surgical procedure.

We claim:

1. A surgical instrument comprising a hollow tube having a longitudinal axis, an inner rod having proximal and distal ends and extending through said hollow tube, handle means for imparting reciprocal movement to said inner rod relative to said hollow tube, a working tip attached to said distal end, a collet coaxial with said hollow tube and reciprocal with respect thereto, a locking pin connected to said inner rod, an attachment housing connected to said hollow tube and being coaxially disposed with respect to said inner rod, said locking pin comprising a locking notch, said locking notch engaging a portion of said attachment housing in an interlocked relationship, said collet comprising a bevelled edge, and a portion of said locking pin disposed in sliding engagement with said bevelled edge.

2. A surgical instrument according to claim 1 wherein said working tip comprises a pair of jaws.

3. A surgical instrument according to claim 1 wherein said handle means is of ergonomic configuration.

4. A surgical instrument comprising a hollow tube having a longitudinal axis, an inner rod having proximal and distal ends and extending through said hollow tube, handle means for imparting reciprocal movement to said inner rod relative to said hollow tube, a working tip attached to said distal end, said handle means comprising a pair of handles, a locking rod engageable with said handle means and comprising elongated inner and outer portions, one of said portions being of smaller diameter than the other of said portions, each of said portions being of substantially uniform diameter throughout its entire length, and said locking rod being moveable a limited distance such that in one position one of said handles is disengageable with respect to said one of said portions and in another position is interlocked with respect to said other of said portions.

5. A surgical instrument according to claim 4 wherein said locking rod is spring biased.

6. A surgical instrument according to claim 4 wherein a partially closed ring is formed on said one of said handles and wherein said partially closed ring cooperates with said locking rod.

7. A surgical instrument comprising a hollow tube having a longitudinal axis, an inner rod having proximal and distal ends and extending through said hollow tube, handle means for imparting reciprocal movement to said inner rod relative to said hollow tube, a working tip attached to said distal end, said hollow tube and said inner rod being disjointably interconnected, a collet coaxial with said hollow tube and reciprocal with respect thereto in a direction parallel to the axis of said hollow tube, a locking pin connected to said inner rod, an attachment housing connected to said hollow tube, said locking pin and said attachment housing being disjointably interconnected, said collet comprising a bevelled edge, and a portion of said locking pin disposed in sliding engagement with said bevelled edge.

* * * * *